United States Patent
Terentiev

(10) Patent No.: US 6,494,613 B2
(45) Date of Patent: Dec. 17, 2002

(54) APPARATUS AND METHOD FOR MIXING MATERIALS SEALED IN A CONTAINER UNDER STERILE CONDITIONS

(75) Inventor: Alexandre Terentiev, Lexington, KY (US)

(73) Assignee: Levtech, Inc., Lexington, KY (US)

( * ) Notice: Subject to any disclaimer, the term of this patent is extended or adjusted under 35 U.S.C. 154(b) by 0 days.

(21) Appl. No.: 10/068,373

(22) Filed: Feb. 5, 2002

(65) Prior Publication Data

US 2002/0105856 A1 Aug. 8, 2002

Related U.S. Application Data

(60) Provisional application No. 60/266,651, filed on Feb. 6, 2001.

(51) Int. Cl.[7] .................................................. B01F 7/16
(52) U.S. Cl. ........................................ 366/279; 366/343
(58) Field of Search ................................ 366/279, 285, 366/308, 342, 343, 118, 326.1; 383/127; 604/416, 408; 206/219

(56) References Cited

U.S. PATENT DOCUMENTS

| | | | |
|---|---|---|---|
| 370,549 A | * 9/1887 | Lochner et al. ............. 366/279 |
| 1,579,382 A | * 4/1926 | Mitchell ..................... 15/141.1 |
| 2,641,412 A | * 6/1953 | Byberg ....................... 366/326.1 |
| 2,877,994 A | * 3/1959 | Jones ......................... 366/326.1 |
| 3,045,988 A | * 7/1962 | Briscoe ....................... 366/285 |
| 3,311,354 A | * 3/1967 | Wilson ........................ 366/248 |
| 3,647,397 A | * 3/1972 | Coleman ................... 366/167.1 |
| 4,355,906 A | 10/1982 | Ono |
| 5,183,336 A | 2/1993 | Poltorak et al. |
| 5,193,977 A | * 3/1993 | Dame .......................... 277/634 |
| 5,362,642 A | * 11/1994 | Kern ............................ 222/94 |
| 5,533,804 A | 7/1996 | Larsson et al. |
| 5,578,012 A | 11/1996 | Kamen et al. |
| 5,938,325 A | * 8/1999 | Edwards ................... 366/326.1 |
| 5,941,635 A | * 8/1999 | Stewart ..................... 366/165.5 |
| 6,071,005 A | * 6/2000 | Ekambaram et al. ........ 604/416 |
| 6,234,666 B1 | * 5/2001 | Kolb ........................... 366/279 |

OTHER PUBLICATIONS

"The FLEXBOY Mixer," www.stedim.com. No date, 3 pages.

\* cited by examiner

*Primary Examiner*—Tony G. Soohoo
(74) *Attorney, Agent, or Firm*—King & Schickli, PLLC

(57) ABSTRACT

A mixing bag usable in chemical and bioprocessing procedures that is hermetically sealed about a tube that is closed within the bag but extends out through a seal and adapted to receive a rotatable rigid rod of a predetermined shape for mixing the materials in the bag.

16 Claims, 2 Drawing Sheets

APPARATUS AND METHOD FOR MIXING MATERIALS SEALED IN A CONTAINER UNDER STERILE CONDITIONS

CROSS REFERENCES TO RELATED APPLICATION

This application claims priority from U.S. Provisional Application Serial No. 60/266,651 filed Feb. 6, 2001, and relates to disposable containers used in the biopharmaceutical processing industry. The entire disclosure contained in U.S. Provisional Application Serial No. 60/266,651 is incorporated herein by this reference.

BACKGROUND OF THE INVENTION

The present invention relates to hermetically sealed bags contained products used in the pharmaceutical and biotechnology processing industries and, more particularly, to the mixing of the such products while in situ within the sealed bags.

Bags containing typically fluids under highly sterile conditions are used in the bioprocessing industry for the formulation, storage, transfer and transport of fluid while maintaining the sterile conditions. Some of the characteristics of the bags to preserve the quality of the products contained within include biocompatability with the products, sterility, and non-pyrogenicity. In the biopharmaceutical processing industry, various bioprocessing steps need to be performed within bags to assure proper sterilization for the elimination of the risk of cross-contamination. The use of such bags permitting these processing steps eliminates certain otherwise necessary manual operations and thus reduce the risk of cross-contamination. In addition, the bag sealed after the addition of product eliminates the risk of airborne contamination and potentially harmful oxygen exposure. Thus the bags, typically disposed after use are a recognized efficient means to prepare and store sterile fluids. Generally, these disposable bioprocessing bags are flexible and made from compatible plastic that is sterilized by Gamma radiation. The bags can be used for all bioprocessing applications including, but not limited to, formulating, filing, storing and transporting final product, stocking pharmaceuticals in cold storage or deep freeze and finally for sampling and analytical purposes. Additionally, the bags may be used for biological fluids such as serum, buffers, and ultrapure water and also for growing cell cultures to obtain the valuable biopharmaceutical compounds produced by cells.

In many instances of the products introduced into the bags may need mixing before use. For example, the product may be formulated from the blending of dry powder into a fluid. In other situations, the product may separate during transport or storage time and require mixing before use. Finally, mixing or agitation of the product may be required for the further development of cell cultures.

There are two prior art systems that mix product within a bioprocessing bag. One utilizes non-invasive wave agitation. To accomplish this, the bioprocessing bag is placed in a pan and subject to a controlled rocking motion. This wave agitation creates wave motions within the sealed bag to produce product homogeneity. Another mixing apparatus utilizes a peristaltic pump that squeezes the disposable bioprocessing bag in order to agitate and mix the product within the bag.

The rocking action mixing apparatus typically works best with small volumes and frequently proves to be unsatisfactory for tough mixing situations such as with the dissolving of powders. Often the powders are incompletely placed into a homogeneous solution unless the apparatus is operated for unacceptable lengths of time. The squeezing action of the peristaltic pump can crush living cells through the pressure it applies to the tube to induce circulation. Because each of the bags has a seal at one end, the movement caused by the rocking and/or peristaltic action may cause failure of the seal, allowing contaminants to enter the bag.

It is therefore a paramount object of the present invention to provide a simple, yet effective apparatus and method for mixing materials into final non-contaminated product in sterilized disposable bags. The present invention addresses and corrects problems of the prior art and provides benefits beyond those contemplated by the use of either the wave mixing system or the peristaltic pump system.

This and other objects and advantages of the present invention will become apparent upon a reading of the following description and appended claims.

SUMMARY OF INVENTION

The present invention pertains to a biprocessing bag that contains a mixing element within that can be rotated or agitated without the introduction of contaminants into the bioprocessing bag. The mixing element within the bag includes a flexible tube extending substantially the entire length of the bag. In accordance to one embodiment of the invention, the tube is has a closed distal end within the bag and extends outwardly through a seal and has an open end adapted to accept a more rigid mixing rod of a predetermined shape. The tube is provided with annularly shaped, spaced apart ribs or inserts internally positioned that function to prevent the rigid rod from contacting the tube while it is being threaded into the tube and reduce the friction between the rod and flexible tube. The flexible tube thus takes on the shape of the rod when in position within the tube. The bag is typically placed into a rigid container and clamped about the neck of the bag where the seal is located. The rod is operatively coupled to a drive shaft of a motor and during operation causes the flexible tube to move with the rod for axial or radial mixing of the product contained within the bag. Preferably the shape of the rod is balanced so as not to introduce significant and undesirable vibrations into the bag during operation.

DETAILED DESCRIPTION OF THE PRESENT INVENTION

Figures 1, 1A:
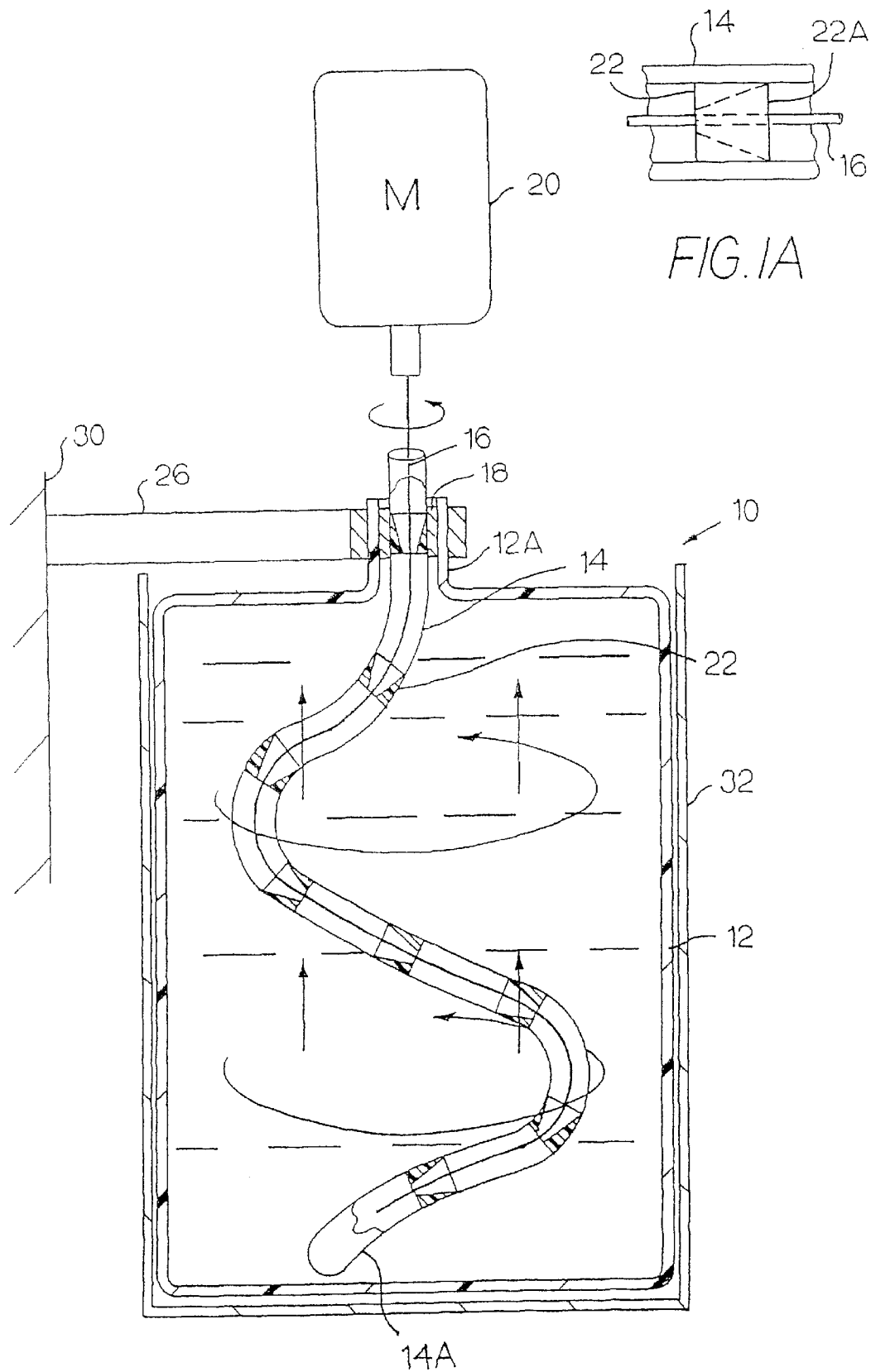
FIG. 1 is a side view shown in schematic form of a first preferred embodiment in accordance with the present invention.
FIG. 1A is an enlarged side view of an insert positioned within the tube showing the conical bore.

Referring first to FIG. 1, the entire mixing apparatus is shown generally by the character numeral 10. The major components of the apparatus are a hermetically sealed flexible bag 12 containing a product typically a fluid. A flexible tube 14 extends through a seal 18 positioned in neck 12A of the bag 12 and has a closed free distal free end within the bag 12. A more rigid rod 16 is threaded the length of the tube 14, provides the shape to the tube 14, and collectively forms the resulting mixing element within the bag. The other end of the rod 16 is coupled to a drive motor 30 for the movement of the mixing element within the bag 12.

During fabrication and before any product is introduced, the bag 12 is sterilized typically by irradiation such as exposure to gamma radiation. The tube 14 and seal 18 are similarly sterilized. Once the bag is filled with product under sterile conditions, the tube 14 and seal 18 are placed in position as shown in FIG. 1, hermetically sealing the bag. The bag 12 then is preferably positioned into a rigid container 32 that functions to hold and stabilize the bag 12. The pressure of the enclosed product within the bag 12 urges the bag against the walls of the container 32 to further give the bag integrity desirable for the mixing operation. Bag 12 can be fabricated from any materials such as, for example, polyethylene that is capable of biomedical use and having the other aforementioned characteristics. The flexible tube 14 is preferably made out of material such as Tygone, although it could be made of other flexible plastic without departing from the spirit or scope of the present invention.

In the embodiment shown in FIG. 1, the tube 14 has an opened distal end, outside the container 12, a closed distal end, inside the container 12 and an essentially a circular cross-section of constant diameter along its length. The static seal 18 positioned in the neck 12A may be fabricated from a rigid plastic such as, for example, polyethylene or other materials such as a ceramic or stainless steels. The important characteristics are inertness and compatibility with the product contained with the bags 12. The actual length of the tube 14 statically positioned within the bag 12 before insertion of the rod 16 depends upon the axial length of the rod 16 to be inserted therein. The rod 16, preferably made of a rigid material such as a metal, is provided a shape that varies depending upon the type of mixing that is desired, i.e., the specifications and bioprocessing demands required to mix the product within the bag 12. It is further preferred that the rod 16 have its mass distributed equally about it axis of rotation to minimize the transfer of vibrations to the product and the apparatus during any mixing process. For radial mixing, a zigzag shape or "S" shape of the rod 16 is the preferred embodiment (as best shown in FIG. 1), although other asymmetrical shapes, such as an inverted question mark (not shown) may be employed when circumstances permit such shapes without departing from the spirit and scope of the present invention.

As illustrated in FIG. 1, it is preferable that the tube 14 be lined with a multiplicity of elastomeric ribs or spacers 22 spaced apart along the length of the inner wall of the tube 14. The spacers function to assist in threading the rod 16 into the tube 14, transferring the movement of the rod 16 to the tube 14 during operation, and to provide more stable shape to the tube 14 while allowing the tube 14 to retain its flexibility. In construction, the diameter of the spacers 22 may be made slightly larger than that of the tube 14 such that when the spacers are positioned within the tube the spacers are tightly forced against the inner wall preventing dislodgment or relative movement thereof during operation. That is, the rotating rod 16 transmits rotational torque energy to the tube 14 through cylindrical spacers 22 without movement of the spacers relative to the axial length of the tube 14. As perhaps best seen in FIG. 1A, the spacers 22 are annular and in one form define a conically shaped bore 22A with the base facing the toward the sealed end of the bag 12. (Alternatively the spacers 22 may be structured to snugly receive inserts having the annular conical shape.) The conical shape of the bore 22a facilitates the feeding or threading of rod 16 through the tube 14 without damage thereto and maintains the rod 16 separate from and in an essentially co-axial relationship with the tube 14. This in turn minimizes vibrations during operation. The spacers are preferably fabricated from a low friction material such as Teflon although in some instances materials such as a non-corrosive metal may be used.

In most instances it is important that the flexible bag 12 be placed into a rigid container such as container 32 shown in FIG. 1. The bag 12 due to its contents then will become stable against the walls of the container 32 and the neck 12A of the bag 12 may be clamped preferably about the seal 18 with a clamp mechanism 26. The clamp mechanism further reduces undesirable vibrations during operation. The clamp mechanism may be secured to any firm infrastructure represented by wall 30 or to the container 32 itself or the support for the motor 20. Threading of the tube 14 with the rod 16 can further occur at this time. Once threading of the rod 16 into the tube 14 has been completed, the flexible tube 14 has taken on the shape of the now inserted rigid mixing rod 16. The free distal end of rod 16 is then coupled or otherwise attached to the drive shaft of the motor 20. After mixing is completed, the rod 16 can be removed from the tube 14 within the bag 12, and the bag 12 along with the other components including the tube 14 and spacers 22 can be moved for further processing as desired. The bag 12 along with tube 14 can be discarded once processing has been completed while the rod 16 can be used again.

Figure 2:
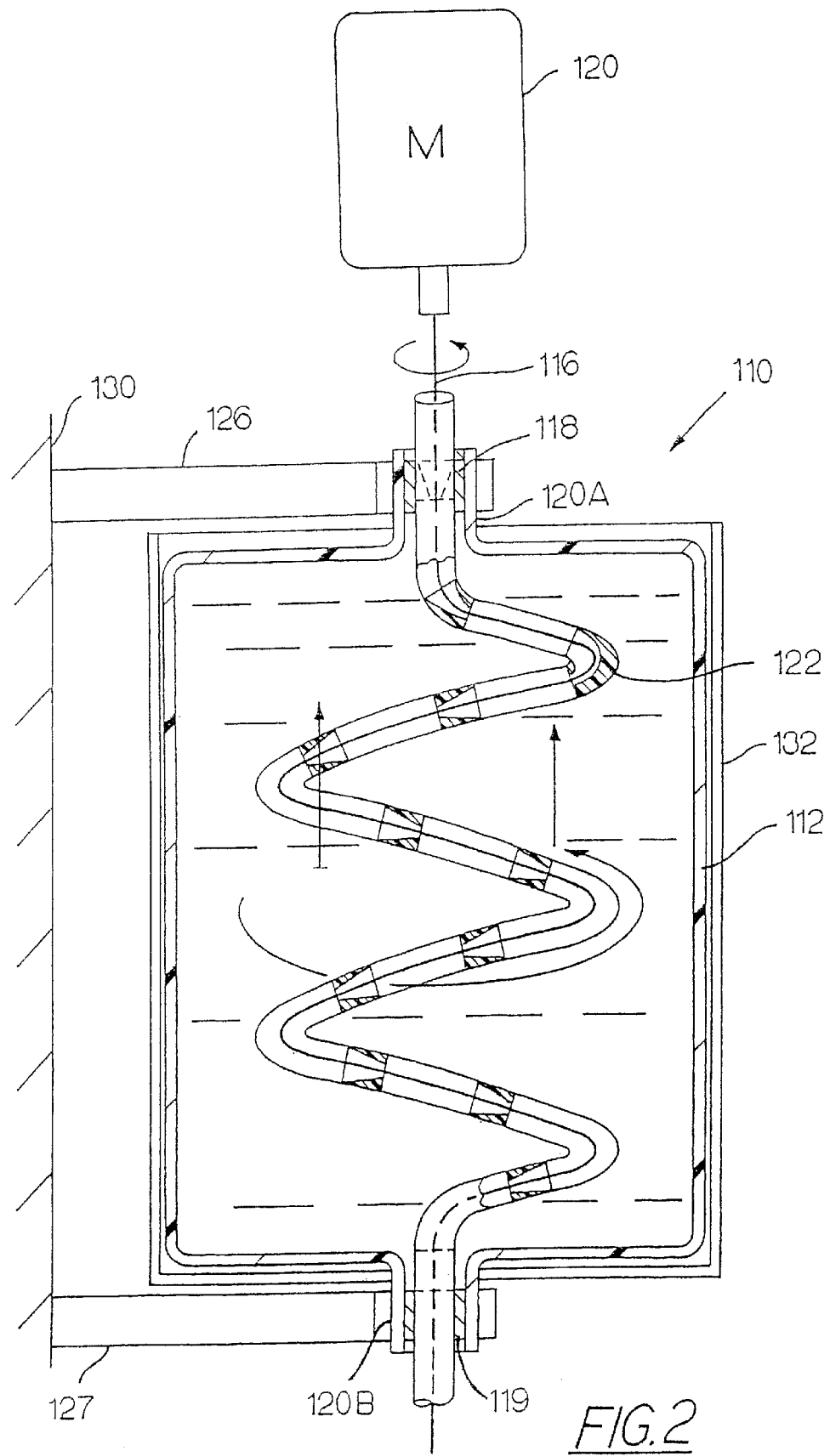
FIG. 2 is a side view of a second embodiment in accordance with the present invention.

Reference is now made to FIG. 2 depicting still another embodiment of the present invention. For clarity like parts are numbered similarly to those shown in FIG. 1 except using three digits. The second preferred embodiment is substantially the same as the first preferred embodiment with the differences in construction accomplishing axial versus radial mixing.

The tube 140 in this embodiment extends completely through the bag 120 through two seals 118 and 119 positioned respectively at the top and bottom ends of the bag 120. As before the seal 118 located at the neck 120A while seal 119 is located at the bottom neck 120B of the bag 120 and the static exit seal 164 is located at the opening in the foot of the container 120B. As with the first preferred embodiments, the static seals 118, 119 can be made out of a rigid plastic similar to polyethylene, ceramic or a metal similar to stainless steel. Both necks 120*a* and 120*b* are clamped by respective clamps 126 and 127 for the same purpose as described above. A helically shaped rigid rod 116 is threaded through the tube 114 as before with the other distal end of the rod 116 extending through the opening in the foot of the bag 112. The mixing operation occurs identically as previously described.

From a reading of the description above in light of the appended drawings, it will be obvious to those with ordinary skill in the art that further modifications and changes may be made to the embodiments described herein without departing from the spirit and scope of the present invention as claimed.

What is claimed is:

1. An apparatus for mixing materials into final non-contaminated product comprising:

a container containing said materials under sterile conditions;

an annularly shaped seal positioned in an opening into said container;

a flexible tube extending through said seal into said container and having a hermetically sealed relationship with said seal, said tube being closed within said container and having an open distal end outside of said container;

a substantially rigid rod positioned within and spaced apart from said tube, said rod have a predetermined shape and substantially spanning the length of said tube within said container; and a motor detachably secured to one end of said mixing rod for rotating said shaft to thereby mix said materials within said container.

2. The apparatus of claim 1 in which said container is a flexible bag.

3. The apparatus of claim 2 in which said flexible bag is positioned within a rigid container and further including a clamping mechanism for holding said bag about the seal.

4. The apparatus of claim 1 in which a multiplicity of annularly shaped spacers are positioned in a spaced apart relationship with said tube, said spacers maintaining said rod in said spaced apart relationship with said tube.

5. The apparatus of claim 4 in which said spacers have a conical shape to facilitate threading of said rod into said tube.

6. The apparatus of claim 5 in which said rod is maintained in an essentially co-axial relation with said tube.

7. The apparatus of claim 5 in which said rod has a shape which is essentially balanced when rotated.

8. The apparatus of claim 5 in which said rod has a S-shape.

9. The apparatus of claim 5 in which said container has a second opening and a second annularly shaped seal positioned within said opening, said flexible tube extending through said second seal and in an hermetically sealed relationship therewith.

10. The apparatus of claim 9 in which said rigid rod has a helically shape within said container and extends the length of said tube and out through said second seal.

11. A hermetically sealed article of manufacture for containing materials under sterile conditions and permitting mixing of such materials comprising a container containing said materials and having at least one opening;

an annularly shaped sealed positioned in said opening; and a flexible tube extending through said opening into said container, said tube being closed within said container and having an open distal end outside of said container, said tube further being provided with a multiplicity of spaced apart annularly shaped inserts along its length and adapted to receive a rigid rod therethrough.

12. The article of manufacture of claim 11 in which said container has a second opening and a second annularly shaped seal in said second opening, said tube extending through said second seal and in hermetically sealed relationship therewith.

13. The article of manufacture of claim 11 in which said container is a flexible bag adapted to be placed into a rigid container for further processing.

14. A method of mixing materials within a container under sterile conditions including the steps of providing a container with an annularly shaped seal in an opening in said container;

placing a closed portion of a flexible tube with annularly shaped inserts spaced along the interior of the tube through said seal and into said container in an hermetically sealed relationship with said seal so that the open end of said tube is outside of said container;

feeding a rigid rod of a predetermined shape through the open end of the tube into said tube through the annular spacers along the length thereof in a spaced apart relationship with said tube and leaving a free distal end of said rod outside of said tube;

clamping said tube to hold said tube stationary at the point; and rotating said rod to cause movement of said tube within said container thereby mixing the materials contained in said container.

15. The method of claim 14 in which said container is a flexible bag and including the further step of placing the bag into a rigid container.

16. The method of claim 14 in which the predetermined shape of said rod is is such that its mass is distributed substantially equally about its axis of rotation thereby minimizing vibrations due to rotation of an unbalanced mass.

* * * * *

UNITED STATES PATENT AND TRADEMARK OFFICE
CERTIFICATE OF CORRECTION

PATENT NO. : 6,494,613 B2
DATED : December 17, 2002
INVENTOR(S) : Alexandre Terentiev It is certified that error appears in the above-identified patent and that said Letters Patent is hereby corrected as shown below:

Column 4,
Line 32, please delete -- 140 --.
Line 37, please delete -- 164 --.
Line 66, please insert -- mixing -- after "rigid."
Line 67, please replace "have" with -- having --.

Column 5,
Line 4, please replace "shaft" with -- rod --.
Line 30, please replace "helically" with -- helical --.
Line 37, please replace "sealed" with -- seal --.

Column 6,
Line 24, please replace "spacers" with -- inserts --.

Signed and Sealed this

Second Day of August, 2005

JON W. DUDAS
*Director of the United States Patent and Trademark Office*